United States Patent
Burel et al.

[19]

[11] Patent Number: 6,036,692
[45] Date of Patent: Mar. 14, 2000

[54] ROD INTRODUCER FORCEPS

[75] Inventors: Marc H. Burel, Towaco, N.J.; David L. Brumfield, Southaven, Miss.; Thomas Barker, Memphis, Tenn.

[73] Assignee: SDGI Holdings, Inc., Wilmington, Del.

[21] Appl. No.: 09/110,993

[22] Filed: Jul. 7, 1998

Related U.S. Application Data

[62] Division of application No. 08/798,091, Feb. 12, 1997, Pat. No. 5,810,878.

[51] Int. Cl.⁷ .................................................. A61B 17/70
[52] U.S. Cl. ................................................ 606/61; 606/207
[58] Field of Search ........................... 606/61, 62, 105, 606/207, 205, 60

[56] References Cited

U.S. PATENT DOCUMENTS

| | | | |
|---|---|---|---|
| 4,411,259 | 10/1983 | Drummond | 600/61 |
| 4,567,884 | 2/1986 | Edwards | 128/69 |
| 4,927,425 | 5/1990 | Lozier | 606/99 |
| 5,020,519 | 6/1991 | Hayes et al. | |
| 5,364,397 | 11/1994 | Hayes et al. | 606/61 |
| 5,423,855 | 6/1995 | Marienne | |
| 5,674,228 | 10/1997 | Henderson et al. | 606/207 |
| 5,817,094 | 10/1998 | Errico et al. | 606/61 |

FOREIGN PATENT DOCUMENTS

| | | | |
|---|---|---|---|
| 2 684 866 | 6/1993 | France | A61B 17/16 |
| WO 91/16020 | 10/1991 | WIPO | A61F 5/00 |

OTHER PUBLICATIONS

*Compact CD Low Back Surgeon's Documentation*, Sofamor Spine Division, pp. 60–61, 78–79.
Cotrel–Dubousset Instrumentation (one page).
The TSRH Implant System, Chapter 2, pp. 50–51.
Universal Spinal System Rod Introduction Pliers by Synthes Spine (13 pages).

*Primary Examiner*—Michael Buiz
*Assistant Examiner*—Kevin Truong
*Attorney, Agent, or Firm*—Woodard, Emhardt, Naughton Moriarty & McNett

[57] ABSTRACT

Forceps are provided with a bifurcated gripping nose on one end adapted to pivotally engage an implant while a rod passes between the branches of the bifurcated gripping nose. The forceps further define a fulcrum adjacent the gripping nose. The pivotally engaging gripping nose and included fulcrum permit a surgeon to urge the rod into an opening in the implant with a single instrument while securely gripping the implant. With the implant pivotally engaged by the gripping nose, movement of the forceps towards the rod brings the fulcrum into contact with the rod and further movement urges the rod into an opening in the implant. In an alternative form, the gripping nose is laterally offset to urge a laterally offset rod into alignment with the implant upon rotation of the forceps.

15 Claims, 4 Drawing Sheets

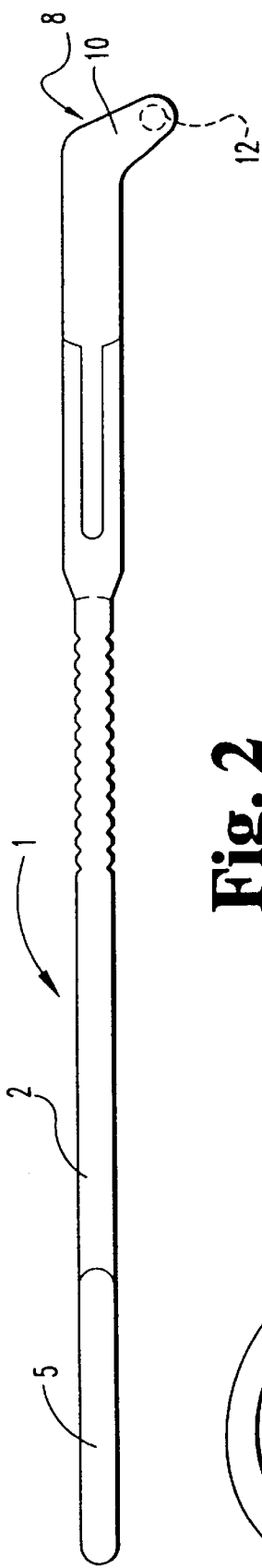
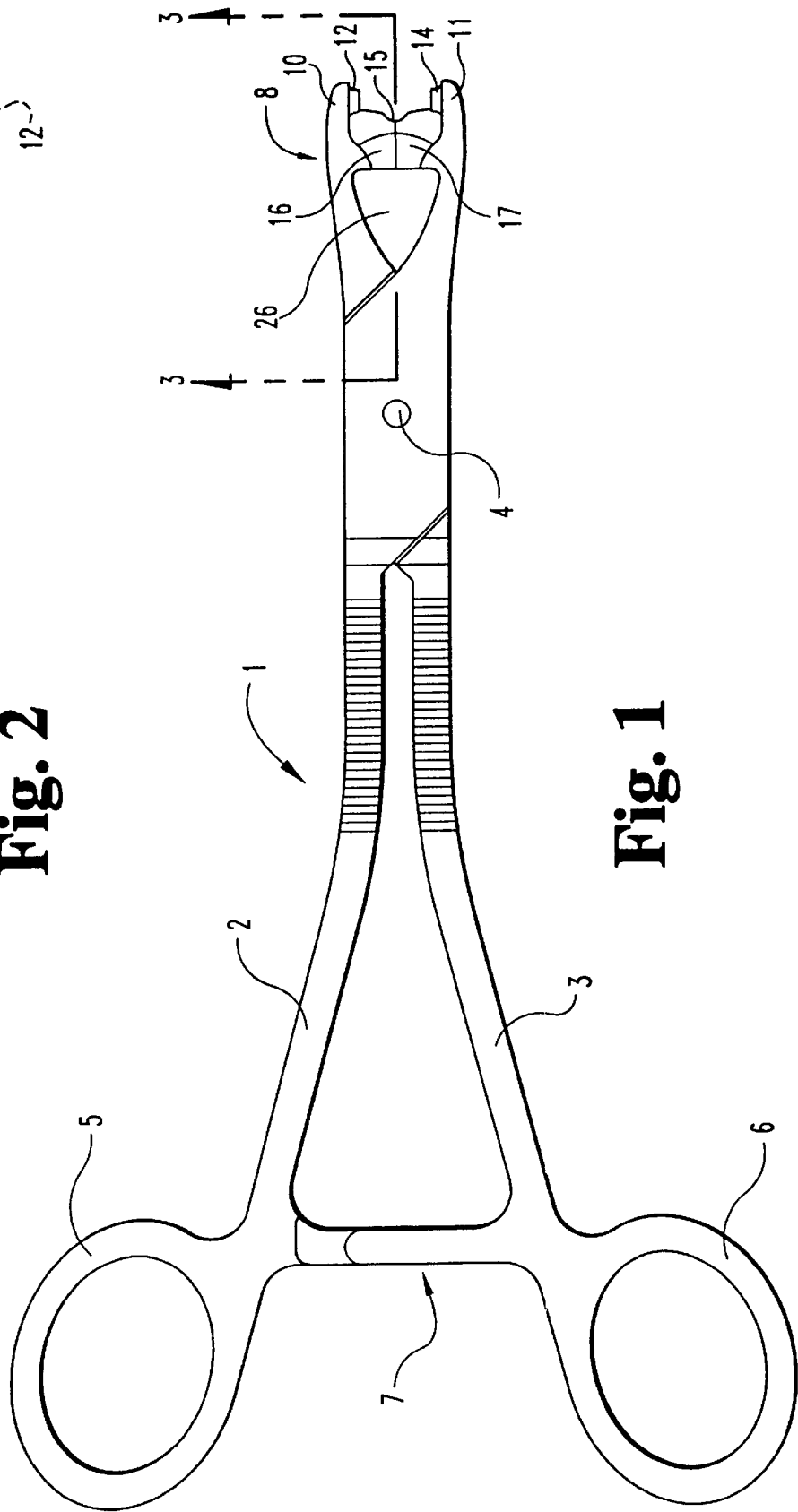

ROD INTRODUCER FORCEPS

This application is a division of application Ser. No. 08/798,091, filed Feb. 12, 1997 now U.S. 5,810,878.

BACKGROUND OF THE INVENTION

The present invention relates to devices for achieving spinal correction, in particular, mechanisms for urging a spinal rod into an implant adapted to receive a rod. While the present invention was developed for use in spinal surgery, it may have uses in other areas of medicine as well.

In many applications, particularly those relating to spinal correction techniques, it is desirable to place a series of implants in a patient's spine prior to inserting a longitudinal member (a rod or a plate) along the spine to interconnect the previously placed implants. On occasion, implants may be vertically spaced from the rod or plate and require a mechanical mechanism to bring the rod or plate into contact with the implant. In the instance of a plate, often the implant is a double threaded bolt with a series of bone screw threads anchoring into the bone and a machine threaded post extending through an opening in the plate. A machine threaded nut slightly larger than the opening in the plate may then be threaded onto the threaded post and tightened to bring the implant closer to the plate. For rod systems, a similar arrangement can be utilized whereby the threaded post of the implant extends through a connector attached to the rod. In these systems a nut is used to draw the implant closer to the connector by progressively threading the nut onto the post of the bone bolt.

Alternatively, it is known to provide a rod introducer mechanism that forces the rod and an implant towards each other. In many cases the implant, either a bone screw or spinal hook, includes an open channel to receive the rod. A plug or set screw can be used to close the channel and lock the rod to the implant. In certain surgical techniques a rod is anchored at both ends by at least one implant, resulting in the rod being suspended above a second implant. A mechanism is then required to urge the second implant and rod together to permit connection of the implant to the rod and more particularly to seat the rod within the open channel of the implant. One such instrument marketed by Sofamor Danek Group as part of the Compact CD™ system, is an introducer lever C-6903 which resembles a fork with a pair of offset tines. The tines of this device extend over the vertically spaced rod and under either side of an enlarged portion of the implant. Once in place, the fork handle is moved toward the rod thereby forcing the rod and implant together. One problem with this arrangement is that the fork tines must pass between the implant and the bone, which in many cases may be difficult and may result in damage to the bone. Moreover, the connection between the fork tines and the implant is not a secure engagement and may result in the rod introducer slipping during the procedure of forcing the rod into the implant.

Other types of rod introduction devices have overcome the problems associated with the simple fork device by first achieving a secure attachment to the implant with articulated forceps or the like. Various instruments for gripping and handling implants are commonly known. One such instrument has a pair of articulating branches defining a gripping nose opposite a pair of handles. While many varieties of these forceps exist to accomplish various functions during surgery, some are adapted specifically to securely hold an implant, and in particular, a spinal osteosynthesis implant. The gripping nose of one such configuration utilizes a pair of inwardly facing cylindrical projections disposed at the distal end of the gripping nose. The cylindrical projections are adapted to engage corresponding recesses on an implant, thereby providing a secure grip. Because of the small size of many spinal implants and the accompanying difficulty gaining a secure grip with only manual pressure, such forceps are often utilized in the manipulation and placement of the implants.

In addition to providing a nose for gripping implants, many forceps also provide a locking mechanism to hold the forceps in the gripping position once the implant is gripped. A common example is the provision of one half of a ratchet rack on one articulating branch aligned to engage a second half of the ratchet rack on the other articulating branch. Upon movement of the branches towards one another, the separate halves of the ratchet rack come into engagement thereby preventing separation of the articulating branches. As is common with such arrangements, the articulating branches have sufficient flexibility that they may be flexed with respect to one another, thereby disengaging the ratchet racks.

An alternative forcep locking mechanism is disclosed in U.S. Pat. No. 5,423,855 owned by the Sofamor SNC subsidiary of Sofamor Danek Group. This patent shows forceps having an implant gripping nose as previously discussed. In this configuration, the articulating branches are held in the closed position by a spring biased cap disposed on the end of the branches opposite the gripping nose.

In prior systems, once a secure engagement has been accomplished between the forceps and the implant, a separate apparatus is attached between the forceps and the rod. In one such mechanism marketed by Sofamor Danek Group as the TSRH™ mini-corkscrew, a threaded rod is threadedly coupled at one end to the forceps and the other end engages the rod. Rotation of the threaded rod urges the rod and implant towards each other. In another mechanism marketed by Sofamor Danek Group as an articulated rod pusher C-6211 for use with the Compact CD™ system, forceps grip the implant and a pivoting two piece rod pusher lever is used to urge the rod and implant towards one another. In this device, a lower end of the first member of the rod pusher engages the rod and the upper end of the first member is pivotally attached to the second member of the rod pusher lever. The lower end of a second member engages the forceps while the upper end of the second member is rotated to force the rod and implant towards each other.

It should be understood that in the various devices described, the implant may move toward the rod, the rod may move or bend toward the implant, or both devices may move towards each other to accomplish the connection. The device which moves depends in large measure on the procedure being performed and the flexibility of the rod utilized. Regardless, each of the prior art mechanisms requires both a device to securely grip the implant and a separate mechanism to apply force to the rod and thereby urge it into the implant. There remains a need for a simple and effective device that accomplishes the desired features of gripping the implant and forcing the rod into the implant.

The present invention overcomes the problems associated with the prior art by providing a gripping mechanism and a rod introduction lever in a single convenient instrument.

SUMMARY OF THE INVENTION

One form of the present invention contemplates a rod introduction forceps for urging a rod into an implant adapted to receive the rod, comprising a first branch having a first terminal end, a second branch articulated with the first branch, the second branch having a second terminal end, the first and second terminal ends defining a gripping nose, the gripping nose adapted to pivotally engage the implant, and the first and second branch defining a fulcrum for engaging the rod adjacent the gripping nose, whereby pivoting of the first arid second branches about the gripping nose toward the rod causes the fulcrum to urge the rod toward the implant.

Another form of the invention contemplates a rod introduction device for urging a rod into an implant adapted to receive the rod, comprising a device for pivotally attaching to the implant, a fulcrum adapted to engage the rod attached to the device for pivotally attaching, and a lever attached to the fulcrum, whereby movement of the lever about the device for pivotally attaching to the implant forces the fulcrum into contact with the rod and thereby urges the rod into the implant.

Still another form of the present invention contemplates a rod introduction device for urging a rod into an implant adapted to receive the rod, the device comprising a lever having a first end and a second end, a bifurcated gripping nose connected to the first end, the nose adapted to pivotally attach to the implant, and a fulcrum positioned along the lever between the first end and the second end, the fulcrum adapted to engage the rod.

Additionally, the invention includes a method for urging a rod into an implant, comprising the steps of providing a lever having a fulcrum and an implant gripping nose defining a passage for a rod and adapted to pivotally engage the implant, attaching an implant to a body part, placing a rod adjacent the implant, positioning the rod in the passage in the implant gripping nose, gripping the implant with the gripping nose, rotating the lever about the pivotal engagement at the implant and toward the rod, thereby urging the fulcrum against the rod and the rod into the implant, securing the rod in the implant, and removing the lever.

An object of the present invention is to provide forceps that pivotally grip an implant and provide a fulcrum for urging a rod into an implant.

A further object of the present invention is to provide rod introduction forceps that urge a rod into an implant without additional mechanisms to generate the urging force.

Still a further object of the present invention is to provide a method of introducing a rod into an implant utilizing an instrument that both grips the implant and forces the rod into the implant.

Another object of the present invention is to provide rod introduction forceps with a rod bearing surface that allows controlled introduction of the rod into an implant.

An additional object of the present invention is to provide a lever and fulcrum combination that can be pivotally and securely engaged with an implant. The lever and fulcrum combination being operable to urge a rod into an implant.

Still a further object of the invention is to provide a lever and fulcrum combination that upon rotation provides both lateral approximation of an laterally offset rod and vertical approximation of a vertical offset rod.

Related objects and advantages of the present invention will be apparent from the following description.

BRIEF DESCRIPTION OF THE DRAWINGS

FIG. 1 is a top plan view of an embodiment of the rod introducer forceps of the present invention.

FIG. 2 is a side view of the rod introducer forceps of FIG. 1.

DESCRIPTION OF THE PREFERRED EMBODIMENTS

Figure 3:
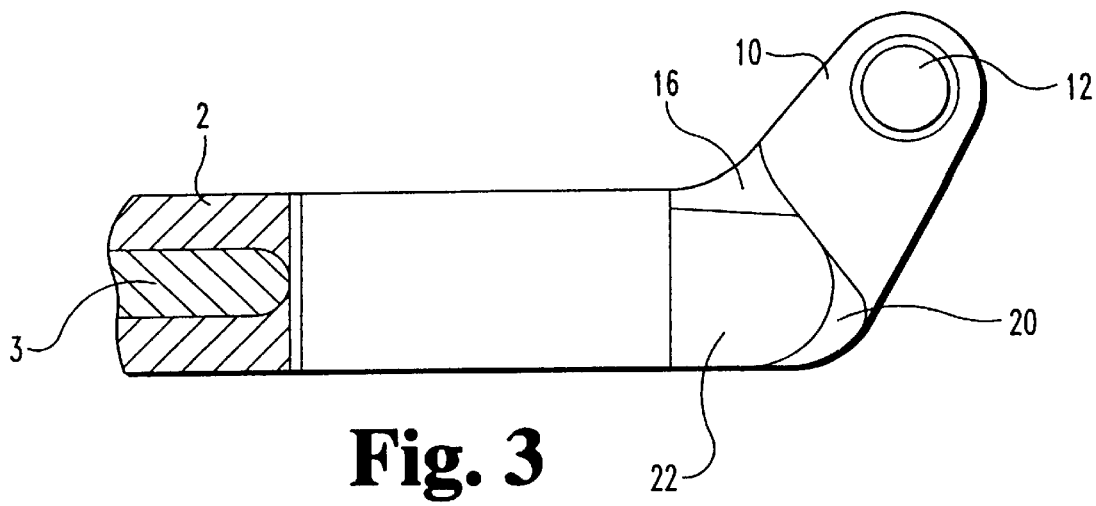
FIG. 3 is a cross-sectional view taken along section lines 3—3 of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Figure 6:
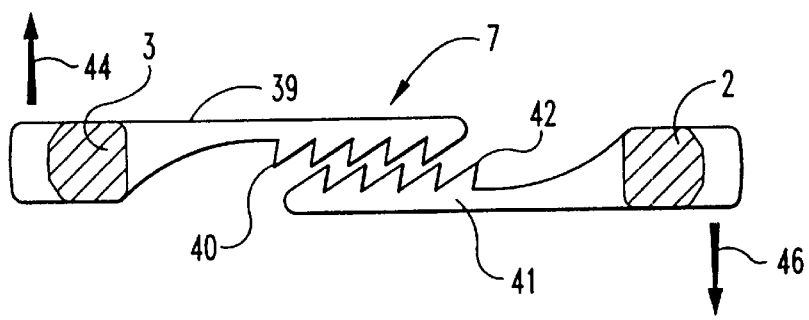
FIG. 6 is a partial cross-section view of the rod introduction forceps of FIG. 1 showing the ratchet mechanism.

Referring now to FIG. 1, a rod introduction forceps 1 according to the present invention includes a first branch 2 articulated with a second branch 3 about transverse pin 4. Branches 2 and 3 are provided with handles 5 and 6, respectively, to control the articulating movement of the branches with respect to each other. Disposed between the articulating branches and adjacent handles 5 and 6, is a conventional ratchet mechanism 7 (FIG. 6.) for maintaining the forceps in a closed gripping position as shown in FIG. 1. Branch 2 includes a ratchet rack 41 having multiple teeth 42. Correspondingly, branch 3 has an opposing ratchet rack 39 having a plurality of ratchet teeth 40. As articulating branches 2 and 3 are moved towards the closed gripping position, ratchet teeth 40 and 42 interengage to prevent spreading of branches 2 and 3 after the user releases handles 5 and 6. Branches 2 and 3 have sufficient flexibility that when it is desired to release ratchet mechanism 7, the branches may be moved in the directions of arrows 44 and 46 (FIG. 6) respectively, thereby disengaging ratchet teeth 40 and 42 and permitting articulating branches 2 and 3 to be moved apart. It is understood that other locking mechanisms are within the contemplation of the present invention provided they provide the desired characteristics.

It is conventional for forceps to be provided with a bifurcated gripping nose opposite the handles. In the present invention, as shown in FIG. 2, bifurcated gripping nose 8 is defined by each end of branches 2 and 3 opposite handles 5 and 6 and is offset with respect to the longitudinal axis of the articulating branches. Offset gripping nose 8 is comprised of a first gripping nose extension 10 connected at its base to branch 3 and having an inwardly facing cylindrical projection 12 disposed adjacent its distal tip. The other half of offset gripping nose 8 is comprised of gripping nose extension 11 connected at its base to branch 2 and having a complimentary inwardly facing cylindrical projection 14 disposed adjacent its distal tip and aligned with cylindrical projection 12. Cylindrical projections 12 and 14 are provided to pivotally engage corresponding recesses in an implant. While the projections are shown as cylindrical projections it is contemplated that they could take any form, provided they securely engage the implant. Alternatively, it is within the contemplation of the present invention that the implant could be provided with projections to be received in corresponding indentations in the gripping nose.

According to the present invention, rod introduction forceps 1 further includes a left fulcrum extension 16 and a right fulcrum extension 17 provided at the base of gripping nose extensions 10 and 11, respectively. Between fulcrum extensions 16 and 17, and transverse pin 4 is an open area 26 with no contact between the articulating branches. Left and right fulcrum extensions 16 and 17 each define a portion of recessed area 15. As explained further herein, recessed area 15 is configured to engage a spinal rod to be inserted in a spinal implant. Gripping nose extensions 11 and 10 extend a sufficient distance from branches 2 and 3 respectively, to grip an implant and provide clearance between the implant and fulcrum extensions 16 and 17 to permit passage of a rod which is elevated with respect to the implant (see FIGS. 4 and 7). It is understood that the amount of force that can be applied at fulcrum extensions 16 and 17 is dependent on the amount of force applied to handles 5 and 6 and the length of branches 2 and 3, which operate as a lever in the present invention.

Referring now to FIG. 3, a cross-sectional view taken along section lines 3—3 of FIG. 1, there is illustrated gripping extension 10 extending away from the longitudinal axis of branches 2 and 3. Further, fulcrum extension 16 includes a contact surface 22 which contacts a corresponding surface on fulcrum extension 17, thereby prohibiting further movement of gripping nose extensions 10 and 11 toward one another. Preferably, the contact surfaces are calibrated to contact when the projections 12 and 14 are fully seated within the implant recesses.

Figure 4:
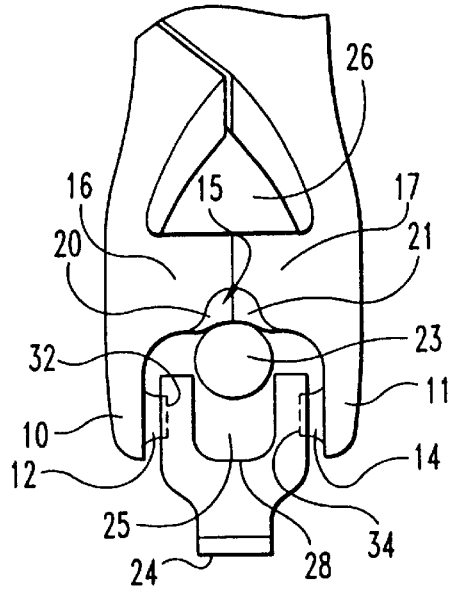
FIG. 4 is a partial perspective view of the gripping nose of the rod introduction forceps of FIG. 1 gripping a spinal implant shown in a rear plan view.
Figure 5:
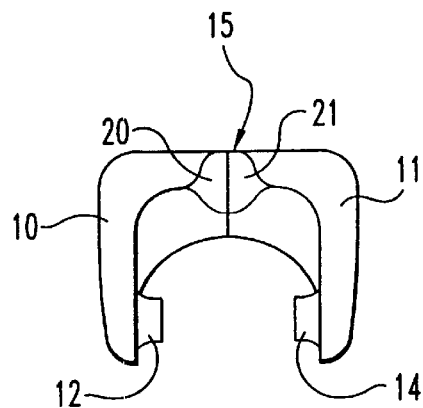
FIG. 5 is a right-side plan view of the gripping nose of the rod introduction forceps of FIG. 2.

In the preferred embodiment, rod bearing surface 20 cooperates with rod bearing surface 21 on fulcrum extension 17 to define rod opening 15, a channel for pivotal engagement of the rod when urging the rod into the implant. As shown in FIG. 3, rod bearing surface 20 has a convex curvature such that as rod introduction forceps 1 rotate about cylindrical projections 12 and 14, a line of contact 70 with rod 23 (FIG. 7) moves along rod bearing surfaces 20 and 21. Additionally, as shown in FIGS. 4 and 5, rod bearing surfaces 20 and 21 also define a concave curvature extending transverse to the line of contact 70. In the preferred embodiment, the concave curvature of rod bearing surfaces 20 and 21 are adapted to engage or seat rod 23 and limit lateral movement of the rod. Although a separate fulcrum extension is shown in the preferred embodiment, it is contemplated that other segments of the forceps may operate as the fulcrum.

Referring now to FIG. 4, a spinal hook 24 suitable for implantation in a human spine is illustrated having attachment recesses 32 and 34 shown in dashed lines. Spinal hook 24 further includes a rod channel 25 adapted to receive spinal rod 23. Spinal hook 24 is shown for illustrative purposes and is not intended to limit the scope of the invention in any way, it being contemplated and intended that the introduction forceps of the present invention may be utilized with various types of implants, including but not limited to screws and hooks implanted in the spine.

Figure 7:
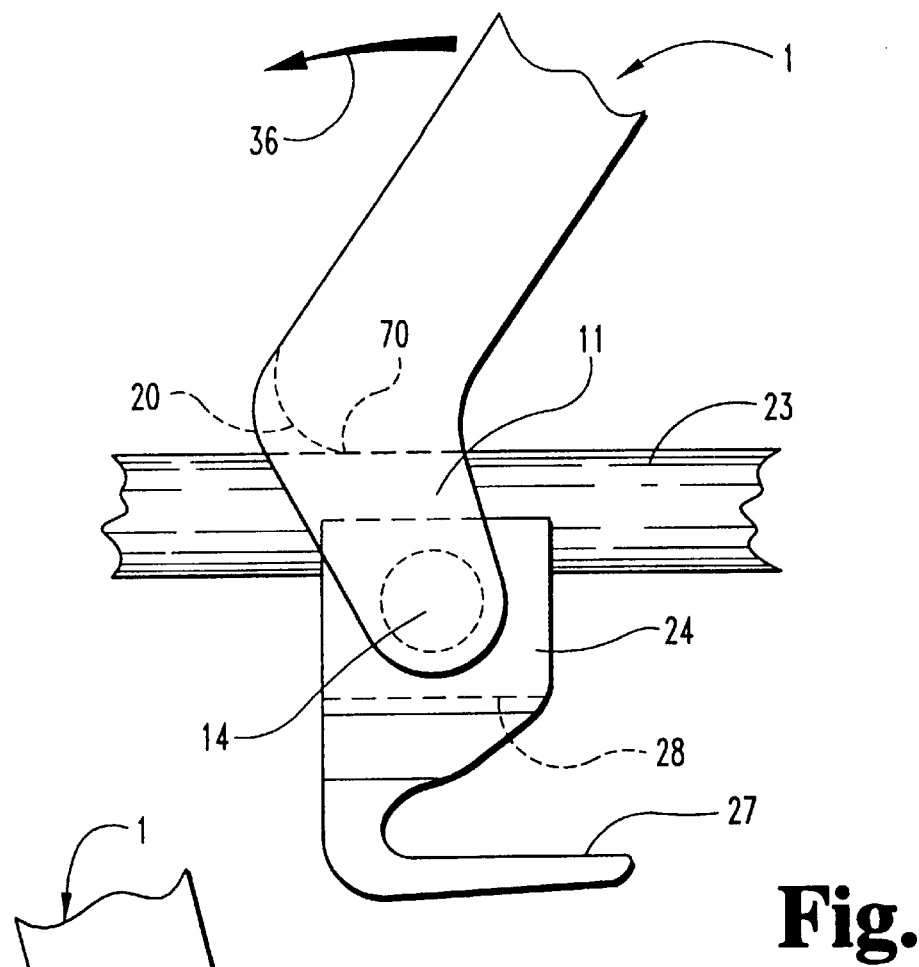
FIG. 7 is a diagrammatic view of the rod introduction forceps gripping nose of FIG. 1 attached to a spinal implant with the rod positioned above the spinal implant.
Figure 8:
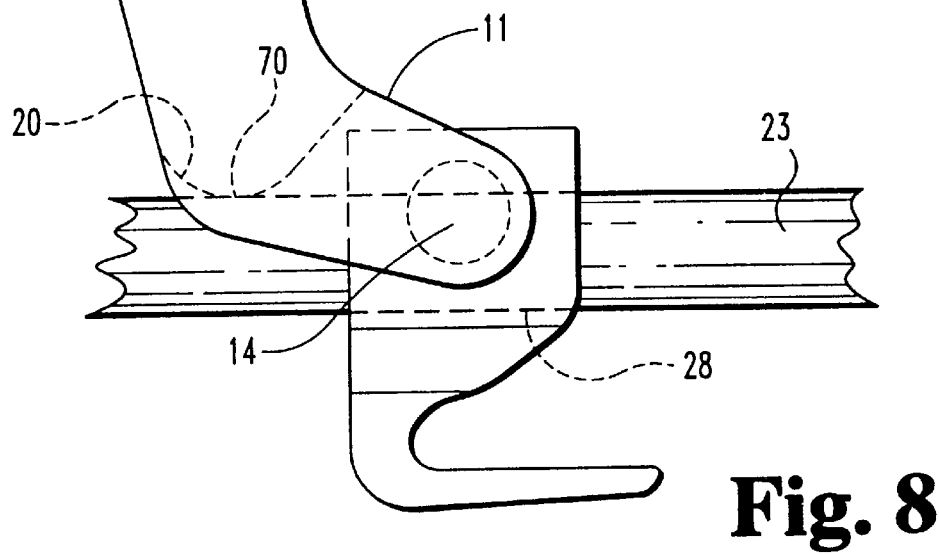
FIG. 8 is the same as FIG. 7 except that the rod has been urged into the spinal implant.

Referring now to FIGS. 7 and 8 showing a portion of rod introduction forceps 1 engaged with spinal hook 24 and rod 23 suspended above spinal hook 24. It is understood, but not illustrated, that often rod 23 is held at either end by additional implants which prevent the rod from easily reaching the bottom of implant 24. Thus, a device is required to force the rod to the bottom 28 of the rod channel 25.

In operation, articulating branches 2 and 3 are urged toward one another, thus urging gripping nose extensions 10 and 11 towards one another to thereby lodge cylindrical extensions 12 and 14 into corresponding recesses 32 and 34 in spinal hook 24 (FIG. 4). Ratchet mechanism 7 maintains articulating branches 2 and 3 in a closed gripping position such that cylindrical projections 12 and 14 are maintained in recesses 32 and 34, respectively. This pivotal engagement permits rod introduction forceps 1 to pivot about the recesses in spinal hook 24 while projections 12 and 14 securely attach the rod introduction forceps to the implant and prevent longitudinal or lateral movement. Moreover, fulcrum extensions 16 and 17 are spaced a sufficient distance from cylindrical projections 12 and 14 to provide clearance above the implant and to permit capturing of rod 23 suspended above spinal hook 24.

Referring now to FIG. 4, implant 24 is securely fastened to a vertebral body (not shown) and rod 23 is positioned over channel 25. Offset gripping extensions 10 and 11 are then passed over rod 23 until cylindrical projections 12 and 14 are aligned with spinal hook indentations 32 and 34, respectively. Once in alignment, pressure is applied at handles 5 and 6 to articulate branches 2 and 3 towards the closed gripping position, thereby forcing projections 12 and 14 into indentations 32 and 34, respectively. As has been previously described, movement of branches 2 and 3 toward one another causes ratchet teeth 40 of ratchet rack 39 to engage ratchet teeth 41 of ratchet rack 41, thereby preventing movement of branches 2 and 3 away from each other until ratchet mechanism 7 is disengaged.

Referring now to FIG. 7, it is illustrated that with the rod introduction forceps 1 pivotally attached to spinal hook 24, rod introduction forceps 1 are rotated about spinal hook 24 in the direction of arrow 36, thereby bringing rod bearing surfaces 20 and 21 into contact with rod 23. Branches 2 and 3 of the rod introduction forceps operate as a lever to apply downward force to the fulcrum. Further rotation of rod introduction forceps 1 in the direction of arrow 36 urges rod 23 into rod channel 25 until rod 23 reaches the bottom 28 of the channel. As shown in FIGS. 7 and 8, contact point 70 between rod 23 and bearing surfaces 20 and 21 moves along bearing surfaces 20 and 21 as the rod introduction forceps 1 are rotated in the direction of arrow 36.

With the rod introduction forceps rotated in the direction of arrow 36 to securely hold rod 23 at the bottom 28 of implant 24, a fastening device (not shown), such as a threaded plug, may be inserted into rod channel 25 to securely hold the rod in position. Once the fastening device is in place, articulating branches 2 and 3 may be moved in the directions of arrows 44 and 46 (FIG. 6) to disengage ratchet mechanism 7. Articulating branches 2 and 3 are then separated, thereby releasing gripping nose 8 from implant 24.

Figure 10:
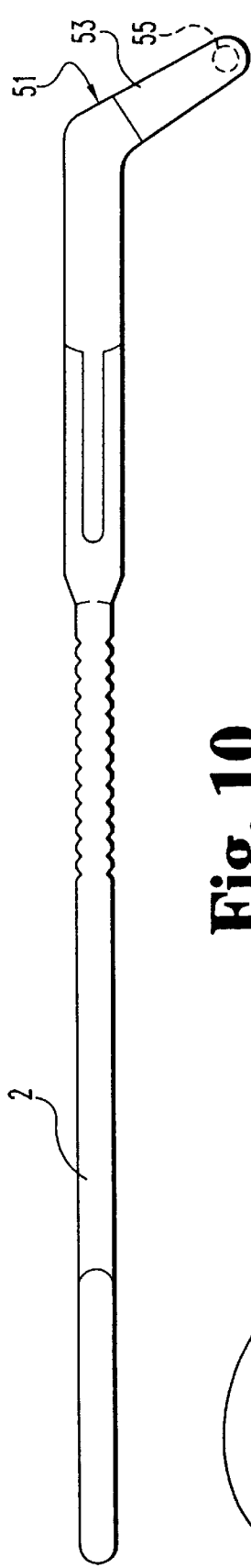
FIG. 10 is a side view of the alternative rod introduction forceps of FIG. 10.
Figure 9:
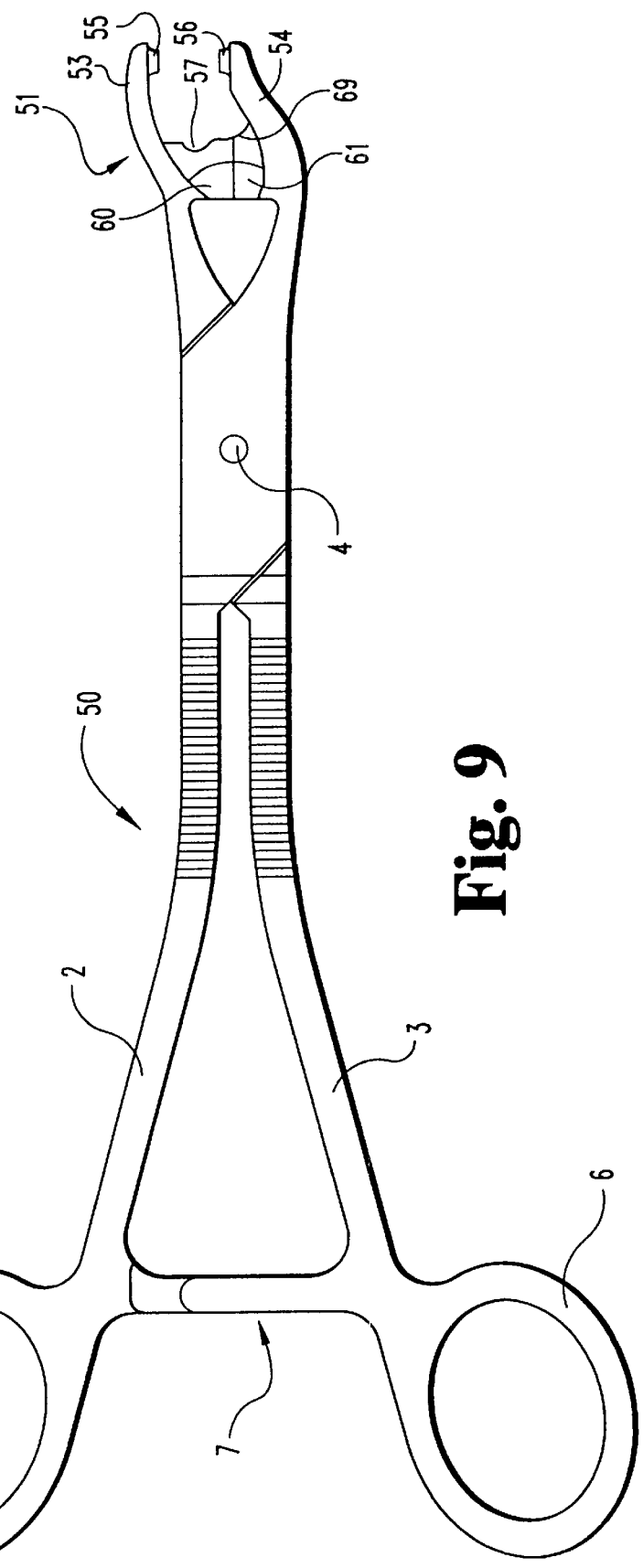
FIG. 9 is a top plan view of an alternative embodiment of the present invention having an angled gripping nose for providing lateral approximation.

In some applications, the rod is laterally offset with respect to the implant. Therefore, it is desirable to have the offset gripping nose laterally angled with respect to the articulating branches of the rod introduction forceps to urge a laterally offset rod into alignment with the implant. Additionally, some applications require that the gripping nose extensions be of greater length to provide additional clearance between the fulcrum and the implant. Referring now to FIGS. 9 and 10, there is illustrated an alternative embodiment of the present invention. FIG. 9 shows rod introduction forceps 50 having articulating branches 2 and 3 with handles 5 and 6, respectively. Additionally, as earlier disclosed, a ratchet mechanism 7 is disposed between articulating branches 2 and 3. The distal end of articulating branches 2 and 3 is formed into laterally angled, offset gripping nose 51. Gripping nose extensions 53 and 54 laterally angle away from the longitudinal axis of rod introduction forceps 50 and terminate in inwardly facing cylindrical projections 55 and 56, respectively. Angled gripping nose extensions 53 and 54 permit the implant to be gripped with a laterally offset rod positioned between the articulating branches. At the base of angled gripping extensions 53 and 54, is provided fulcrum extensions 60 and 61, respectively. Between gripping extension 54 and fulcrum extension 61 is lateral bearing surface 69. As the forceps are rotated about cylindrical projections 55 and 56, a laterally offset rod positioned between gripping extension 53 and 54 will bear against lateral bearing surface 69 to urge the rod into lateral alignment and into rod bearing surface 57. Unlike the embodiment shown in FIG. 1, rod introduction forceps 50 have the rod bearing surface 57 entirely in fulcrum extension 60 so that it will be laterally aligned with the opening in the implant when.

Although the above described rod introduction forceps are shown as the preferred embodiment of the present invention, it should be understood that it is contemplated that the invention could be utilized with any type of forceps mechanism. Additionally, while a forceps mechanism has been disclosed and discussed, it is also contemplated that the implant could be configured, such as by providing a keyway, to pivotally engage a non-articulating gripping nose. Thus, articulating branches would not be required.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Rod introduction forceps for urging a rod into an implant adapted to receive the rod, comprising:
   a first branch having a first terminal end;
   a second branch articulated with said first branch, said second branch having a second terminal end, said first and second terminal ends defining a gripping nose, said gripping nose adapted to pivotally engage an implant; and
   said first and second branches defining a fulcrum for engaging a rod, whereby pivoting of said first and second branches about said gripping nose toward said rod causes said fulcrum to urge the rod toward the implant.

2. The rod introduction forceps of claim 1, wherein said first branch and said second branch have a longitudinal axis and said gripping nose is offset with respect to said longitudinal axis.

3. The rod introduction forceps of claim 2, wherein said gripping nose includes at least one projection adapted to be received in a cooperable recess in said implant.

4. The rod introduction forceps of claim 3, wherein said at least one projection is cylindrical.

5. The rod introduction forceps of claim 1, wherein said first terminal and said second terminal ends each include a projection cooperable with corresponding recesses in the implant to pivotally engage the implant.

6. The rod introduction forceps of claim 5, wherein said projections are cylindrical.

7. The rod introduction forceps of claim 1, further including a ratchet mechanism attached between said first and second branches, said ratchet mechanism maintains said first and second branches in a closed gripping position until released.

8. The rod introduction forceps of claim 1, wherein said fulcrum includes a recess for engaging said rod.

9. The rod introduction forceps of claim 8, wherein said recess is a concave surface having a radius of curvature corresponding to the approximate external diameter of said rod to be implanted.

10. The rod introduction forceps of claim 1, wherein said fulcrum has a longitudinal axis substantially parallel to said rod to be implanted and further including a longitudinal convex curve defining a bearing surface extending along said longitudinal axis, whereby upon insertion of said rod into said implant a point of contact between said rod and said fulcrum moves along said longitudinal bearing surface.

11. The rod introduction forceps of claim 1, wherein said first branch and said second branch have a longitudinal axis and said gripping nose is laterally offset with respect to said longitudinal axis, said first branch including a lateral bearing surface for engaging the rod, whereby pivoting of said first and second branches about said gripping nose toward said rod causes said lateral bearing surface to urge the rod into lateral alignment with the implant.

12. A rod introduction device for urging a rod into an implant adapted to receive the rod, said device comprising:
   a lever having a first end and a second end;
   a bifurcated gripping nose connected to said first end, said nose adapted to pivotally attach to an implant; and
   a fulcrum positioned along said lever between said first end and said second end, said fulcrum adapted to engage a rod to urge the rod into an implant adapted to receive the rod.

13. The rod introduction device of claim 12, wherein said lever includes a longitudinal axis and said bifurcated gripping nose is offset with respect to said longitudinal axis.

14. The rod introduction device of claim 12, wherein said bifurcated nose includes a pair of diametrically opposed branches spaced to receive an implant therebetween, each branch having an interior surface defining a projection thereon, said projection adapted to be received by a corresponding indent in said implant.

15. The rod introduction device of claim 12, wherein said lever includes a first branch and a second branch articulated with said first branch, each of said first and second branches defining a portion of said bifurcated gripping nose and fulcrum.

* * * * *